United States Patent [19]

Eisen

[11] Patent Number: 5,125,424
[45] Date of Patent: Jun. 30, 1992

[54] DEVICE FOR CLEANING TEETH AND/OR GAPS BETWEEN THE TEETH

[76] Inventor: Ewald Eisen, Hofelbeetstr. 10, Heidenheim, Fed. Rep. of Germany, 8824

[21] Appl. No.: 674,950

[22] Filed: Mar. 26, 1991

[30] Foreign Application Priority Data

Mar. 26, 1990 [DE] Fed. Rep. of Germany ... 9003517[U]

[51] Int. Cl.⁵ ............................................. A61C 15/00
[52] U.S. Cl. .................................. 132/323; 132/324; 132/328
[58] Field of Search ............... 132/309, 323, 328, 324, 132/325, 326, 327; 433/146, 147

[56] References Cited

U.S. PATENT DOCUMENTS

| | | | |
|---|---|---|---|
| 691,581 | 1/1902 | Baumeister | 132/323 |
| 806,300 | 12/1905 | Sorenson | 132/323 |
| 893,345 | 7/1908 | Monson | 132/323 |
| 1,306,998 | 6/1919 | Dimitroff | 132/325 |
| 1,666,877 | 4/1928 | Cummer | 132/324 |
| 2,837,098 | 6/1958 | Sorboro | 132/324 |
| 3,368,553 | 2/1968 | Kirby | 433/146 |
| 4,051,857 | 10/1977 | Zambito | 132/323 |
| 4,817,642 | 4/1989 | Lipp | 132/324 |

FOREIGN PATENT DOCUMENTS

| | | | |
|---|---|---|---|
| 2922824 | 12/1979 | Fed. Rep. of Germany | 132/323 |
| 2180753 | 4/1987 | United Kingdom | 132/323 |

Primary Examiner—Cary E. O'Connor
Attorney, Agent, or Firm—Bacon & Thomas

[57] ABSTRACT

The present invention concerns a device for cleaning teeth or gaps between teeth and comprises a handle to hold the device and an operative part, mounted at the end of the handle, with a filamentary or tape-shaped cleaning medium acting on the teeth and/or the teeth gaps when the device is being used. To assure intensive cleaning specially in the molar zone, the operative part is supported at the handle in a pivoting manner about an axis fixed relative to this handle and is guided by the teeth gap during cleaning. The fastening system preferably is such that the operative part is exchangeable in the handle. The operative part is a dental-floss holder comprising a bail with a segment of filamentary dental floss affixed between its free-end legs. The bail is supported at the handle about an axis essentially perpendicular to the longitudinal extent of the dental-floss filament.

19 Claims, 4 Drawing Sheets

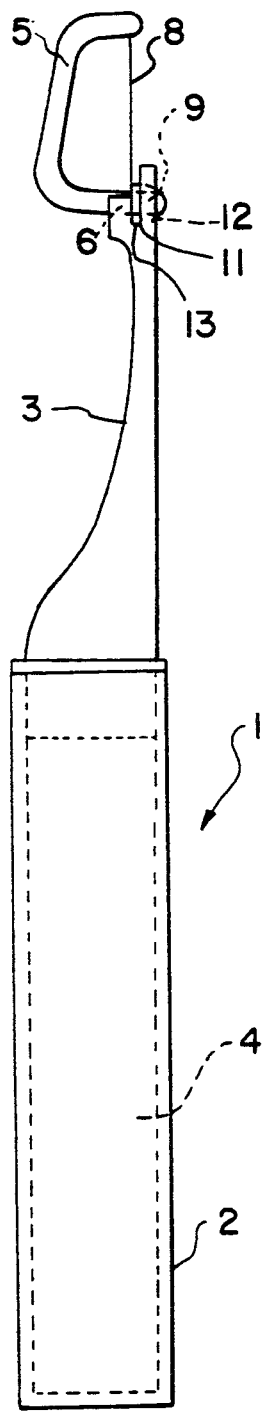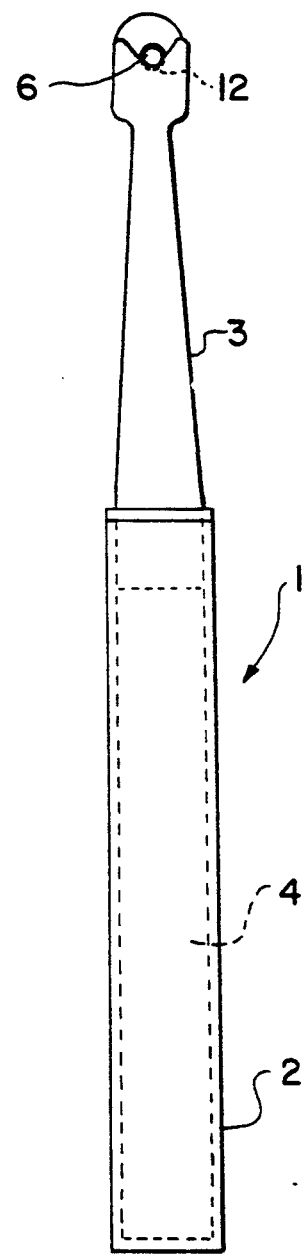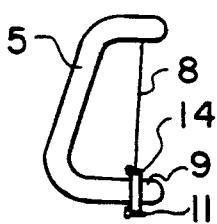

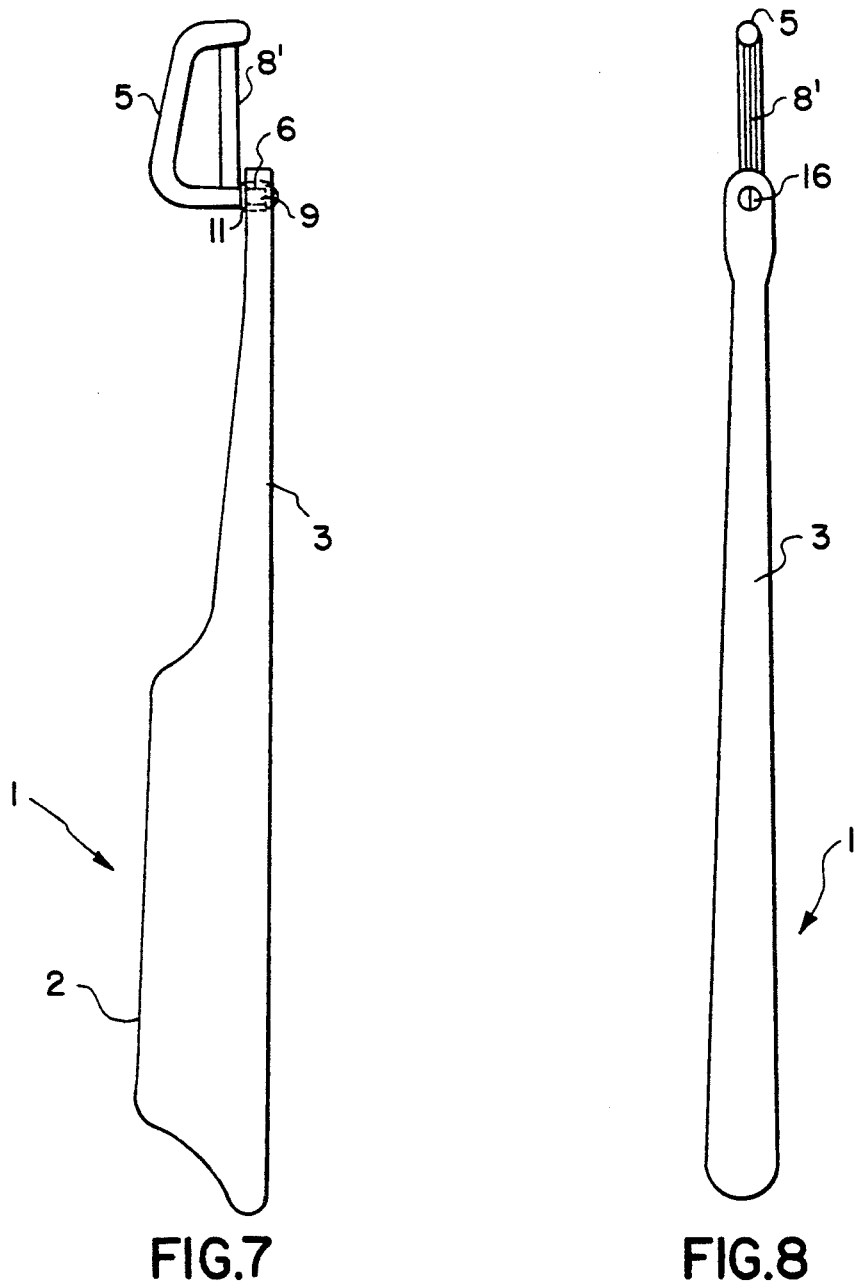
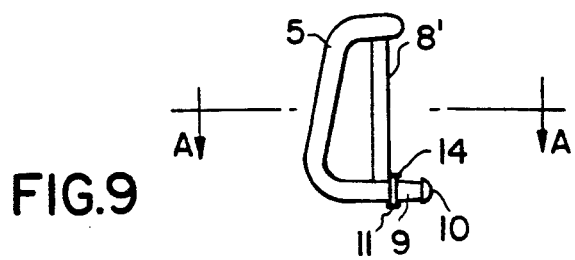
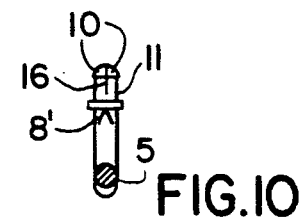

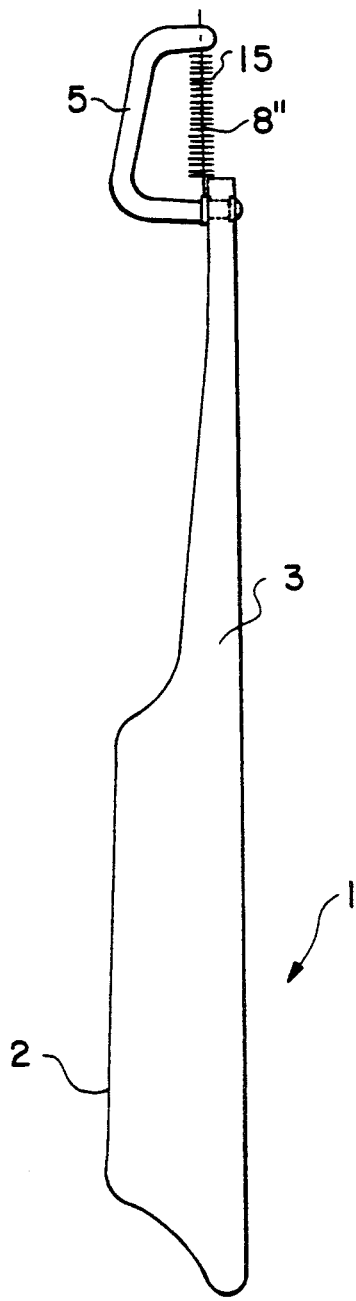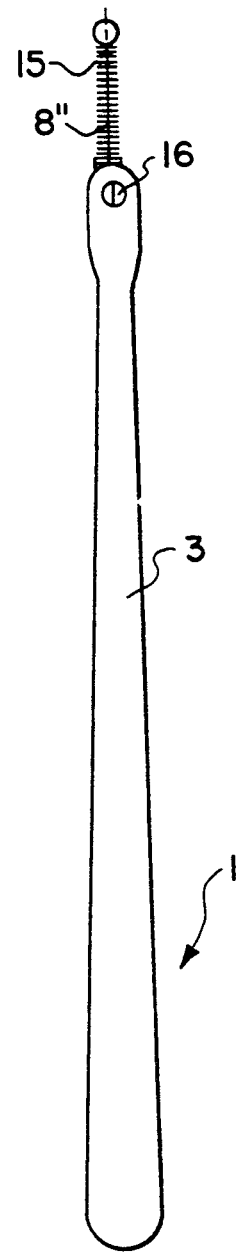
FIG. 11  FIG. 12
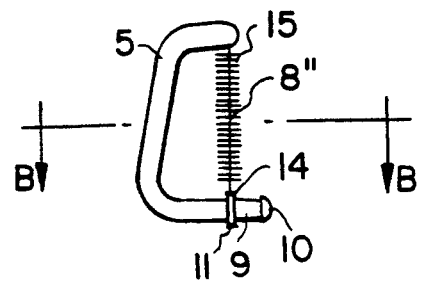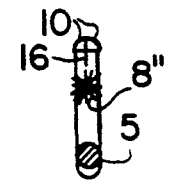
FIG. 13  FIG. 14 under the edge of the first borehole secure the longer leg against axial displacement in the borehole.

DEVICE FOR CLEANING TEETH AND/OR GAPS BETWEEN THE TEETH

BACKGROUND OF THE INVENTION

The invention concerns a device for cleaning teeth or the gaps between teeth of human dentitions, which comprises a handle to hold the device and an operative part at the end of this handle and fitted with a filamentary or tape-shaped cleaning medium that, following activation of the device shall act on the teeth and/or the gaps between the teeth.

Devices of this kind, e.g. illustrative dental-floss holders, are known wherein the handle is rigidly connected to the operative part and, as a result, the cleaning of the molar zone of the dentition can be carried out only with difficulty with the required thoroughness and at every necessary site. When cleaning the gaps between teeth in the molar zone, it will be mandatory to act from all sides on the teeth gaps in view of the especially high danger of caries and gum inflammations in that zone.

SUMMARY OF THE INVENTION

Accordingly it is the object of the invention to create a device for cleaning teeth or teeth gaps of human dentitions and of the initially cited kind whereby foremost also teeth and teeth gaps in the molar zone shall be well accessible everywhere and thereby shall be cleaned especially efficiently.

This problem associated with the prior art is solved by the invention in that the operative part is held at the handle so as to pivotable about a fixed axis and in that the operative part shall be guided by the teeth gap during the cleaning. The cleaning medium, illustratively the dental floss, in this process provides the guidance for the pivotably supported operative part. These two steps make it possible not only to clean gaps between the incisors but also it becomes possible, by suitably pivoting the operative part relative to the handle, to conveniently access the molars or all the gaps between teeth in the molar zone and to clean them. Because the pivot axis is fixed, the compression required during cleaning, especially when sweeping over the entire height of the particular teeth gap, shall be ensured.

In an appropriate embodiment of the invention, the operative part is held in exchangeable manner on the handle and therefore a multi-purpose implement can be created that, when exchanging an operative part, assures a multiplicity of cleaning (brush, floss etc.). On the other hand, if the operative part is worn or soiled, it may be exchanged in a simple manner.

In a further embodiment of the device of the invention, the cleaning medium is a segment of dental floss and the operative part is the dental-floss holder. As previously stated, rigid floss holders are already known in practice. They substantially restrict the use of floss which alternatively may be bought as filaments wound on spools. This follows because when using such a spool, the floss is conventionally wound around two fingers to hold it and then it is tensioned by suitably moving these fingers apart. Therefore a long floss segment is needed for each cleaning of the teeth gaps. On the other hand only a short filamentary floss is needed to affix the floss to a floss-holder, and this floss moreover may be used several times. Because the operative part in the present invention is a floss holder pivotably held on the handle, the gaps in the molar zone—which are especially threatened by caries—can be cleaned in especially efficient manner: On account of the pivotability of the floss-holder, all directions of motions of the floss can be carried out relative to the tooth being cleaned, in particular in the molar zone, which would be nearly impossible in conventional manual cleaning with dental floss.

An especially effective design, which is easily put into practice and therefore leads to simple manufacture is characterized in that the dental-floss holder comprises a bail with a segment of filamentary floss affixed, and preferably tensioned between the bail's free leg ends, this bail furthermore being pivotably mounted by one of the legs on the handle at an axis which is essentially orthogonal to the longitudinal axis of the dental floss filament. So to speak, the dental floss is the continuation of the handle and on account of the pivotable connection between handle and floss holder, it can be pivoted almost over a range of 360°.

Advantageously again, a first handle segment shall be widened into a broadened grip and shall be followed by a second segment in the form of a tapered stem the free end of which holds the floss-holder. This facilitates handling the device because the widened grip is easier to grab than a thin stem, only the latter being inserted together with the floss holder into the mouth.

A further appropriate embodiment of the present invention calls for the widened grip evincing a predetermined preferred extension and the pivot shaft to pivot the operative part, i.e. the floss holder, extending along said longitudinal extension.

In one preferred embodiment, the first handle segment and its second segment are detachably plugged into one another. Thereby the advantage of independently replacing either segment for instance in the event of damage is achieved. Preferably the first handle segment is hollow inside so it may for instance receive replacement bails. Advantageously the cavity shall be closed by the second handle segment sealing the cavity of the first segment when both segments are plugged together. Advantageously the cavity in the first handle segment is at least as long as the second segment inclusive of the floss holder, whereby upon detaching the segments from each other the second one can be housed in the cavity of the first one. Following use of the device, the handle stem therefore can be inserted and kept in the first handle segment.

In a preferred embodiment, one of the legs of the bail is longer than the other. In this case the free end of the longer leg can be used to affix the floss holder and the floss filament can be held in such manner that the free end of the shorter leg projects only slightly beyond the floss filament. Preferably a first borehole is present at the stem end facing the grip to affix the longer leg, with the first borehole receiving a plugged-in end segment of the longer bail leg. In this manner the bail can be easily mounted on the stem without having to apply a large force and it can be removed similarly easily.

In a preferred embodiment, the end segment of the longer bail leg is slitted, several projections being present at the free tip of the end segment that project from the first borehole and reach underneath the edge. In this embodiment the end segment of the longer leg can be elastically compressed in such manner that it is easily passed through the first borehole in the stem and so that the leg end, when released, shall again spread apart elastically, whereby the leg is firmly seated in the borehole. The projections reaching underneath the edge prevent the bail from being forced out of the borehole when the teeth are being cleaned—on account of the forces then acting on this bail.

If the slitted end segment evinces a larger diameter in its relaxed state than the borehole, then this bail can be clamped into that borehole. If furthermore the first borehole is adjoined at the stem end away from the handle by a larger second borehole receiving the projections of the longer bail end segment, then the bail will be prevented from being forced out of the borehole without the projections interferingly extending beyond the stem back side. If furthermore an annular shoulder is formed away from the free tip at the end segment of the longer leg, then this annular shoulder forms a stop preventing bail slippage.

In a further preferred embodiment, the first borehole is open toward the free stem end, the second borehole is slanted, and a vertical slit the size of the ring shoulder thickness is present between the boreholes. This design allows fastening the bail to the stem in such a way that the free leg tip is inserted into the slanted borehole and the annular shoulder is placed into the slit between the boreholes. Thereupon the bail is secured against slippage while nevertheless being easily removed by being tipped over.

In a further embodiment of the device of the invention, it is possible to stop the pivoting motion of the dental-floss holder or the toothbrush holder. The pivoting motion is not degraded thereby, merely some preferred pivoted positions are created that can be adjusted or changed either before cleaning or during it. For instance, the inside of a molar sub-zone can be cleaned with the pivoting motion stopped firmly, for instance the motion of the floss holder toward the handle.

This stopping effect appropriately is achieved in that in the connection region, that is in the region of the pivot axis between the floss holder or toothbrush holder and the handle, at least one beak shall be provided which elastically engages a notch. This design assures a given retention at a stop position, such stopping being eliminated when the force applied exceeds the retaining force. This retaining force must be construed in such manner that it can be exceeded in relation to the requirements either during cleaning or simply before it, that is, the pertinent stop is adjustable. In this respect a number of beaks may be appropriately provided at the side of the annular shoulder that enter matching recesses in the front stem zone.

Because the end segment of the leg connected to the handle projects from the lower side of the stem end away from this handle, mere pressing on the projecting stem end assures that the bail holding the floss can be removed in a simple way.

In a further embodiment of the device of the invention, the dental floss used swells in the presence of moisture or is an impregnated kind.

In a further embodiment of the invention, in lieu of dental floss, the cleaning medium is a preferably folded tape which is regularly used manually especially by dentists to create gaps between teeth, for instance after making a filling.

In a further embodiment of the invention the teeth can be cleaned using a preferably impregnated textile tape as the cleaning medium.

In a further appropriate embodiment of the invention, in lieu of floss or folded tape, the cleaning medium may be an inter-dental brush.

The invention will now be described in detail with reference to various embodiments depicted in the drawings.

BRIEF DESCRIPTION OF THE DRAWINGS

FIG. 4 is a sideview of the device shown in a second embodiment, FIG. 5 is a sideview of the dental-floss holder of FIG. 4, FIG. 6 is a topview of the handle of FIG. 4, FIG. 7 is a sideview of the device of the invention shown in a further embodiment using an operative part designed as a tape holder, FIG. 8 is a topview of the lower side of the device of FIG. 7, FIG. 9 is a sideview of the tape holder of FIG. 7, FIG. 10 is an elevation of the tape holder along the sectional line A—A in FIG. 9, FIG. 11 is a sideview of the device of the invention shown in a further embodiment using an operative part in the form of an inter-dental brush holder, FIG. 12 is a topview of the lower side of the device of FIG. 11, FIG. 13 is a sideview of the inter-dental brush holder of FIGS. 11 and 12, and FIG. 14 is an elevation of the tape holder along the sectional line B—B of FIG. 13.

DETAILED DESCRIPTION OF THE INVENTION

Figure 1:
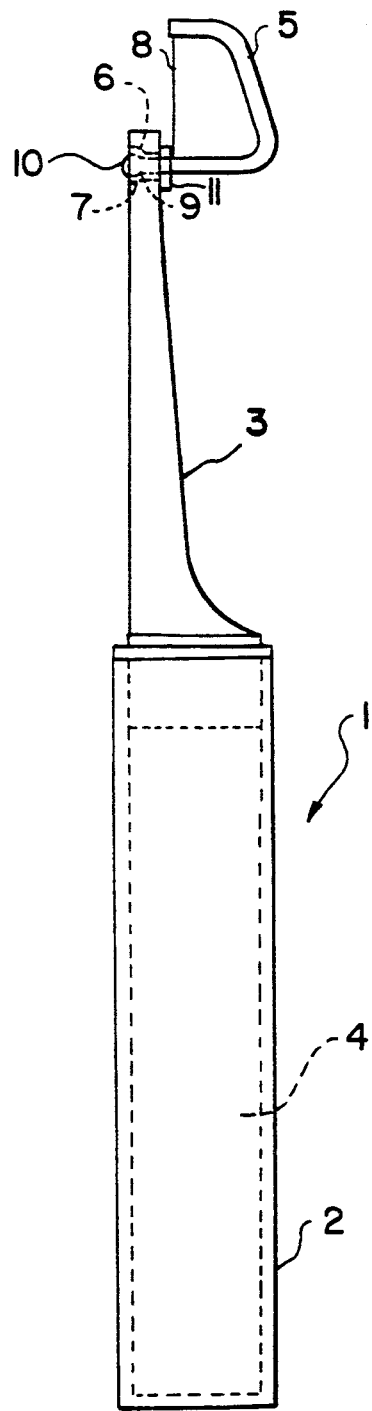
FIG. 1 is a sideview of the device of the invention shown as a first embodiment using a dental-floss holder as the operative part.
Figure 2:
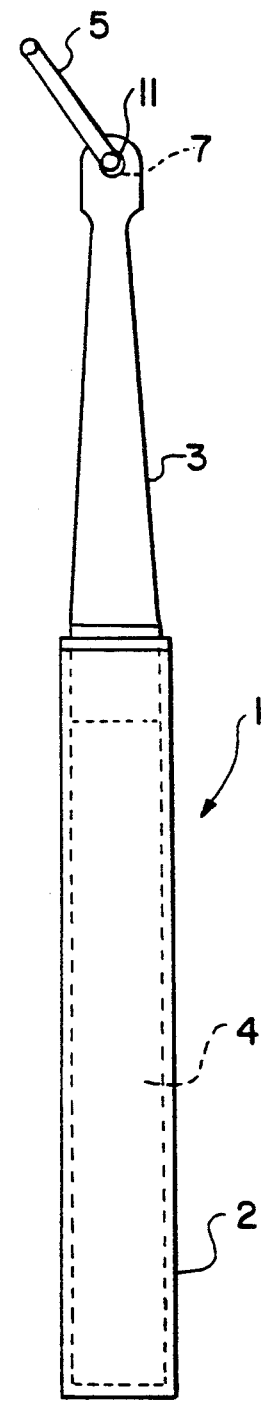
FIG. 2 is a topview of the device of FIG. 1 with a pivotably mounted dental-floss holder.

The device handle 1 is divided as shown by FIGS. 1 and 2 into a widened grip 2 and a tapered stem 3 which are plugged together in detachable manner. A cavity 4 is present in the grip 2 and is sealed by the widened end of the stem 3. The cavity 4 is long enough that the tapered end of the stem 3 can be plugged into it so that this cavity is sealed by the widened end of the stem 3 and additionally bails 5 can be housed in it. A first borehole 6 is present perpendicularly with respect to the longitudinal axis of the stem 3 at the tapered end of this stem and adjoins a second and wider borehole 7.

Figure 3:
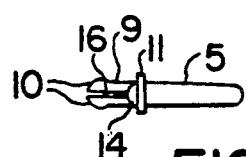
FIG. 3 is a topview of the dental-floss holder of FIGS. 1 and 2.

The bail 5 is pivotably mounted in the boreholes 6 and 7. A segment of filamentary dental floss 8 is tensioned between the free-end legs of the bail 5. One leg of the bail 5 is longer than the other, the end segment 9 of the longer leg of the bail 5 comprising a slit 16 and being somewhat thicker than the borehole 6, also comprising side projections (see FIG. 3). An annular shoulder 11 is present at the end segment 9 of the longer leg of the bail 5 and is a distance from the free leg end. The middle part of the bail 5 is smoothed and it slants toward the shorter leg of the bail 5, whereby impacting the bail 5 against the dentition during cleaning of the teeth gaps will be prevented. The slitted end segment 9 is inserted by compression into the borehole 7 so that the projections 10 come to rest in this borehole. If the bail 5 is released, the slitted tip of the end segment 9 expands elastically, whereby the bail 5 shall be firmly retained in the boreholes 6 and 7 while nevertheless being pivotable about an axis orthogonal to the longitudinal extension of the dental floss.

The device is used in the above described plugged-in state to clean the gaps between teeth. To clean the teeth gaps between the incisors, the bail 5 is rotated in such manner that the floss filament 8 shall be parallel to the longitudinal axis of the handle 1. To clean lateral teeth gaps, the bail 5 is rotated in such a way that the floss filament 8 subtends a suitable angle with the longitudinal axis of the handle 1; to clean the gaps between the rear molars, preferably there shall be a right angle between the floss filament 8 and the longitudinal axis of the handle 1. After cleaning is finished, the bail 5 can be removed from the boreholes 6 and 7 by compressing the end 9 of its longer leg and where called for may be replaced by a new and unused bail. To open the cavity 4, the stem 3 can be separated from the grip 2, whereupon the bail(s) can be stored in the cavity 4 of the grip 2. The grip 2 and the stem 3 can be plugged together in such manner that the tapered end of the stem 3 shall be housed in the cavity 4.

To ensure a stop effect or a snap-in effect for the pivoted position of the bail 5 relative to the stem 3, beaks 14 are provided at the lower side of the annular shoulder 11 which elastically engage (omitted) recesses or notches at the end segment of the stem 3 and which assure a particular stop positions.

Another embodiment is illustrated in FIGS. 4 and 5, which is very similar to the one described above. Therefore identical reference numerals are used for the same or identical components and only the differences are discussed in detail. In this embodiment, the first borehole 6 at the stem 3 is open at the free end of this stem. The second and larger borehole 12 is slanted and a slit 13 as wide as the thickness of the annular shoulder 11 and perpendicular relative to the first borehole 6 is present between the boreholes 6, 12. The end of the leg of bail 5 bearing the annular shoulder 11 is first inserted obliquely into the borehole 12 and then is pivoted into the perpendicular position whereby the leg of the bail 5 also enters the open borehole 6 and the annular shoulder 11 the slit. If the bail 5 is to be exchanged, it must first be tipped into an oblique position so that the annular shoulder 11 shall exit the slit 13. Thereupon the bail can be pulled out in direction of the oblique borehole 12 and be exchanged for a new one. Moreover, the bail 5 in this embodiment just as in the above first one can be pivoted about the axis of the borehole 6 of handle 1. The device is used in the same manner as in the first embodiment.

FIGS. 7 through 14 relate to the description of further and appropriate embodiments resorting to the concept of the invention. Again identical reference numerals shall be used for identical or similar components. Hereafter only the differences relating to the designs of FIGS. 1 through 6 will be discussed in detail.

FIGS. 7 through 10 show a further embodiment of the invention where in lieu of the dental floss there is a tape 8', preferably folded, tensioned between the two bails of the holder 5. As shown by FIG. 10, the edge of the folded tape 8' points to the open side of the bail 5. The ends of the folded tape 18' are rigidly connected in a suitable but omitted manner to the arms of the bail 5. Contrary to the designs of FIGS. 1 through 6, the embodiment of FIGS. 7 through 10 evinces an integral handle 1 in which the flat grip 2, which is flush on account of its flatness with the plane subtended by the bail 5 (when same has not been pivoted), merges integrally into the stem 3. The end segment 9 of the longer leg of the bail 5 also includes a slit 16. The end segment 9 of the bail 5 is inserted into a borehole 6 in order to be affixed to the stem 3, so that the slit 16 is compressed by means of the projections 10 and the end-segment snaps into the borehole 6 as soon as the projections 10 of the end segment 9 have been moved through the borehole. In this case also pivotability of the dental-floss holder is assured relative to handle 1.

In a further embodiment of the device, as shown in FIGS. 11 through 14, an interdental brush 8'"—instead of the filamentary dental floss 8 or the folded tape 8'—is tensioned between the free-end legs of the bail 5. The brush may include a wire or filament mounted to the bail in the manner of the dental-floss filament 8. The bristles 15 are arranged spirally around the wire or filament. Using this brush, the device also may be used to clean large teeth gaps, for instance caused by missing teeth. Otherwise the embodiment matches that of FIGS. 7 through 10.

It should be noted that various changes and/or modifications can be made to the embodiments described above without departing from the spirit of the invention. In general, the invention is intended to be limited only by the scope of the following claims.

I claim:

1. A device for cleaning teeth or the gaps between the teeth, comprising a handle for grasping the device; an operative part disposed at an end of the handle, said operative part including a holder in the form of a bail having a pair of free-end legs, one leg of which is longer than the other leg, for supporting therebetween an elongated cleaning medium which, upon activation of the device, acts on the teeth and/or the gaps between the teeth, said longer leg of the bail including an end segment; and a pivot means for supporting the operative part at the handle in a pivotable manner about an axis fixed in relation to the handle, said pivot means including a first bore hole at said end of the handle supporting said operative part, said end segment of the bail being disposed in said first borehole such that said bail is pivotably supported at the handle substantially orthogonal to the longitudinal extent of the cleaning medium, said operative part being arranged so as to be guided by the teeth gap during cleaning.

2. Device defined in claim 1, including means for supporting the operative part in an interchangeable manner by the handle.

3. Device defined in claim 1, wherein the operative part is of elongated shape and includes means for tensioning a cleaning medium to provide adequate guidance length of the operative part at the teeth gap.

4. Device defined in claim 1, wherein the cleaning medium is a segment of dental floss and in that the operative part is a dental floss holder.

5. Device defined in claim 1, including a first segment of the handle in the form of a widened grip and a second segment of the handle in the form of a tapered stem joined at one end to the first segment and having a free opposite end, said cleaning medium holder being disposed at said free end of said second segment.

6. Device defined in claim 5, wherein the first segment of the handle and the second segment are connected to each other in detachable manner.

7. Device defined by claim 5, wherein the first segment of the handle is hollow and includes a cavity therein.

8. Device defined in claim 7, wherein the cavity has an open end and wherein, in the connected state, the second segment of the handle seals the open end of the cavity.

9. Device defined in claim 7 wherein the cavity in the first segment of the handle is at least as long as the second segment of the handle inclusive of the cleaning medium holder, whereby following separation of the segments, the second segment may be housed in the cavity of the first segment.

10. Device defined in claim 1, wherein said end segment is divided along its length and including side projections provided at the tip of the end segment which project from the first bore hole and engage the far edge of the bore hole.

11. Device defined in claim 10, wherein said end segment has a slightly larger diameter than the first bore hole.

12. Device according to claim 1, including a first bore hole at said end of the handle; said longer leg of the bail including an end segment, said end segment being longitudinally divided and having sideways projections at the tip area of the end segment; a second bore hole larger than the first bore hole adjoining and intersecting the first bore hole; said end segment extruding through both bore holes, with said projections disposed in close fitting relationship in said second bore hole.

13. Device defined in claim 1, including an annular shoulder on the end segment of the longer leg of the bail, said shoulder located inwardly from the tip end of said segment.

14. Device defined in claim 13, wherein said first bore hole comprises an open channel opening away from the handle; a second bore hole disposed in the end of the handle adjacent said first bore hole, said second bore hole being larger than said first bore hole and inclined toward the handle in a direction extending away from the first bore hole; and a slot in the handle extending perpendicular to said first bore hole disposed between said first and second bore holes and corresponding in width to the width of said shoulder, said longer leg of the bail extending through said first and second bore holes and said shoulder disposed in said slot.

15. Device defined in claim 1, including means for stopping pivoting motion of the operative part relative to the handle.

16. Device defined in claim 15, wherein said stopping means includes at least one beak and notch means for providing the stopping effect in the zone between the operative part and the handle, said beak means elastically engaging said notch means.

17. Device defined in claim 1, wherein the cleaning medium is an interdental brush.

18. A device for cleaning teeth or gaps between the teeth, comprising a handle for grasping the device and an operative part disposed at an end of the handle for holding an elongated cleaning medium which, upon activation of the device, acts on the teeth and/or the gaps between the teeth, a pivot means for supporting the operative part at the handle in a pivotable manner about an axis substantially orthogonal to the longitudinal extent of said cleaning medium, said operative part being arranged so as to be guided by the teeth gap during cleaning and includes means for tensioning said cleaning medium to provide adequate guidance length of the operative part of the teeth gap, means for supporting the operative part in an interchangeable manner by the handle, said operative part including a bail having a pair of free-end legs for supporting said elongate cleaning medium between said legs, wherein one of the legs of the bail is longer than the other leg of the bail and said pivot means comprises a first bore hole at said end of the handle supporting said operative part and said longer leg of the bail includes an end segment, which end segment is disposed in said first bore hole in order to pivotally support said bail.

19. A device for cleaning teeth or the gaps between the teeth, comprising a handle for grasping the device, said handle including separable first and second segments, said first segment being formed with a cavity therein; an operative part disposed in the end of the handle including a holder for an elongated cleaning medium which, upon activation of the device, acts on the teeth and/or the gaps between the teeth; and pivot means for supporting the operative part at the handle in a pivotable manner about an axis fixed in relation to the handle, wherein said operative part is arranged to be guided by the teeth gap during cleaning and wherein the cavity in the first segment of the handle is at least as long as the second segment of the handle inclusive of cleaning medium holder, whereby following separation of the segments, the second segment may be housed in the cavity of the first segment.

* * * * *